(12) United States Patent
Snyder et al.

(10) Patent No.: US 10,531,829 B2
(45) Date of Patent: Jan. 14, 2020

(54) SENSOR CHAIN DEVICES AND METHODS

(71) Applicant: NextGen Aeronautics, Inc., Torrance, CA (US)

(72) Inventors: Robert Snyder, Redondo Beach, CA (US); Scott Bland, Hilsborough, NC (US); Robert C DeMott, II, Danville, VA (US)

(73) Assignee: NEXTGEN AERONAUTICS, INC., Torrance, CA (US)

( * ) Notice: Subject to any disclaimer, the term of this patent is extended or adjusted under 35 U.S.C. 154(b) by 726 days.

(21) Appl. No.: 15/152,377

(22) Filed: May 11, 2016

(65) Prior Publication Data

US 2017/0325739 A1    Nov. 16, 2017

(51) Int. Cl.
*A61B 5/00* (2006.01)
*H01B 5/12* (2006.01)
*A61B 5/11* (2006.01)

(52) U.S. Cl.
CPC ............ *A61B 5/6804* (2013.01); *A61B 5/112* (2013.01); *A61B 5/1126* (2013.01); *A61B 5/4528* (2013.01); *A61B 5/725* (2013.01); *A61B 2562/12* (2013.01); *A61B 2562/164* (2013.01)

(58) Field of Classification Search
CPC ....... A61B 5/6804; A61B 5/11; A61B 5/1126; A61B 5/4528; A61B 5/725
USPC ......................................... 600/595; 174/74 R
See application file for complete search history.

(56) References Cited

U.S. PATENT DOCUMENTS

| | | | |
|---|---|---|---|
| 2007/0251570 A1* | 11/2007 | Eckert .................. | H01G 9/2031 136/256 |
| 2010/0041974 A1* | 2/2010 | Ting ..................... | A61B 5/0408 600/388 |
| 2015/0047897 A1* | 2/2015 | Zimet .................... | H02G 3/083 174/521 |

* cited by examiner

*Primary Examiner* — Timothy J Thompson
*Assistant Examiner* — Charles Pizzuto
(74) *Attorney, Agent, or Firm* — Fish IP Law, LLP (57) ABSTRACT

A chain segment having wires that connect various electrical devices and connectors together. The wires are arranged in a pattern to facilitate strain relief. The wires, electrical devices, and connectors are encased in an injection molded material, and they are preferably coupled with a flexible material such as a fabric that can be stitched into a garment. The chain segment facilitates collection of movement data when stitched into an article of clothing. A method of manufacturing the chain segment that is modular to enable different configurations and different lengths of chains.

10 Claims, 10 Drawing Sheets

SENSOR CHAIN DEVICES AND METHODS

FIELD OF THE INVENTION

The field of the invention is sensor chain systems and methods.

BACKGROUND

The background description includes information that may be useful in understanding the present invention. It is not an admission that any of the information provided in this application is prior art or relevant to the presently claimed invention, or that any publication specifically or implicitly referenced is prior art.

Recent and ongoing efforts to measure and evaluate physical performance include the DARPA Warrior Web (WW) and the NSRDEC Personal Augmentation programs. A critical aspect of these and other related efforts is the need for real-time physiological and kinesthetic data on the individual soldier. For instance, the data would be critical for feedback to injury mitigation and performance augmentation devices and for continuous assessment of a person's health and abilities. Also, a detailed database of such information on a large number of people would help tailor devices for each individual, help training, minimize injuries as well as guide future technology development and implementation.

But these solutions fail to create a non-invasive, ultra-lightweight (i.e., barely perceptible to the wearer), low power, minimally wired robust system that provides real-time and stored lower limb kinematics (joint angles and rates) data, with sufficient accuracy and redundancy for a variety of applications.

All publications identified in this application are incorporated by reference to the same extent as if each individual publication or patent application were specifically and individually indicated to be incorporated by reference. Where a definition or use of a term in an incorporated reference is inconsistent or contrary to the definition of that term provided in this application, the definition of that term provided in this application applies and the definition of that term in the reference does not apply.

Thus, there is still a need for improved kinematic measurement systems, methods, and apparatuses.

The following description includes information that may be useful in understanding the present invention. It is not an admission that any of the information provided in this application is prior art or relevant to the presently claimed invention, or that any publication specifically or implicitly referenced is prior art.

SUMMARY OF THE INVENTION

The inventive subject matter provides apparatuses, systems, and methods in which one or more sensors are formed into a chain and used to measure a person's movements. The inventors also contemplate methods of manufacturing a sensor chain. The sensor chains are designed to be flexible such that they can be incorporated into, for example, clothing or other materials that undergo large amounts of strain.

In one aspect of the inventive subject matter, the inventors contemplate a segment of a chain of electrical devices that is semi-flexible. The chain includes an electrical device (e.g., a sensor) and a set of wires coupled to the electrical device. The set of wires are at least partially affixed to a flexible material (e.g., a fabric) to form a pattern to enable strain relief when the flexible material is stretched. The electrical device can be at least partially encased in a first material to protect it from damage, and it can further be encased in a second material to better incorporate it into the segment of the chain of electrical devices.

In some embodiments, the first and second materials can have different material properties (e.g., two different silicones having different hardnesses). The pattern that the wires are set (e.g., affixed to the flexible material) into can be a repeated series of S-shaped bends or a repeated series of Z-shaped bends (or another repeating pattern that enables strain relief). While a repeated pattern can be useful, in other embodiments, the wires can be held into an unpatterned arrangement that does not repeat regularly. This can enable designs to reduce strain in particular portions of the wires where more strain would otherwise be experienced.

In any regard, arranging the wires into a configuration that promotes strain relief ensures that when the wires are stretched, the amount of strain experiences on any particular portion of the wires is not so great that the wires become damaged during the course of stretching and compression of, for example, an article of clothing.

In some embodiments, the set of wires can further be coupled to a connector, which enables the ability to plug in to a device (e.g., a computer, a mobile device, etc.) to upload or download data from one or more electrical devices.

In preferred embodiments, the segment of the chain can include an additional electrical device and an additional set of wires coupled to the additional electrical device. The additional set of wires are at least partially affixed to the flexible material to form a pattern to enable strain relief (e.g., the same pattern as with the other set of wires) when the flexible material is stretched. This additional set of wires can also be coupled to the first electrical device.

In another aspect of the inventive subject matter, the inventors contemplate a method of manufacturing a segment of a chain of electrical devices that is semi-flexible. The method includes the steps of: (1) providing access to a wire mold module and an electrical device mold module; (2) arranging the wire mold module and the electrical device mold module according to a chain design; (3) disposing a set of wires into the wire mold module; (4) disposing an electrical device into the electrical device mold module; (5) coupling the set of wires with the electrical device; (6) injecting a material (e.g., a silicone) into the wire mold module to encase the set of wires in place; and (7) injecting another material (e.g., a silicone having the same or different material properties as the other injected material) into the electrical device mold module to encase the electrical device in place with respect to the set of wires.

In some embodiments, the method additionally includes the step of curing the injection molded materials in a pressure tube. It can also include the steps of arranging a second wire mold module adjacent to the wire mold module, positioning the set of wires in the second wire mold module, and injecting the material (e.g., silicone) into the second wire mold module to encase the set of wires in place.

In some embodiments, the injected materials can be different silicones having different material properties. For example, the material (e.g., silicone) injected into the wire mold module can be softer than the material (e.g., silicone) injected into the electrical device mold module. In other embodiments, the injected materials can have the same material properties.

In other embodiments, the method can include the following additional steps: (1) providing access to a second wire mold module and a second electrical device mold module; (2) arranging the second wire mold module and the second electrical device mold module according to the chain design; (3) disposing a second set of wires into the second wire mold module; (4) disposing a second electrical device into the second electrical device mold module; (5) coupling the second set of wires with the second electrical device and also with the first electrical device; (6) injecting the first material into the second wire mold module to encase the second set of wires in place; and (7) injecting the second material into the second electrical device mold module to encase the second electrical device in place with respect to the second set of wires.

In preferred embodiments, the first wire mold module is made to have a plurality of protrusions to hold the set of wires in a pattern. The same can be true for all wire mold modules. In some embodiments, for example, the pattern is an S-shape and in others the pattern is a Z-shape.

In yet another aspect of the inventive subject matter, the inventors contemplate an article of clothing having a sensor for detecting movements of a wearer. The article of clothing includes a segment of a chain of electrical devices that is semi-flexible and having a set of wires coupled to the sensor where the set of wires are at least partially affixed to a flexible material to form a pattern to enable strain relief when the flexible material is stretched. The flexible material is at least partially affixed to the article of clothing. In preferred embodiments, the flexible material (e.g., a fabric) is at least partially affixed to the article of clothing such that the sensor is located a distance from at least one joint of the wearer.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values in this application is merely intended to serve as a shorthand method of referring individually to each separate value falling within the range. Unless otherwise indicated in this application, each individual value is incorporated into the specification as if it were individually recited in this application. All methods described in this application can be performed in any suitable order unless otherwise indicated in this application or otherwise clearly contradicted by context. The use of any and all examples, or exemplary language (e.g. "such as") provided with respect to certain embodiments in this application is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed in this application are not to be construed as limitations. Each group member can be referred to and claimed individually or in any combination with other members of the group or other elements found in this application. One or more members of a group can be included in, or deleted from, a group for reasons of convenience and/or patentability. When any such inclusion or deletion occurs, the specification is in this application deemed to contain the group as modified thus fulfilling the written description of all Markush groups used in the appended claims.

Various objects, features, aspects and advantages of the inventive subject matter will become more apparent from the following detailed description of preferred embodiments, along with the accompanying drawing figures in which like numerals represent like components.

DETAILED DESCRIPTION

This application is directed to systems, methods, and devices of and relating to a flexible sensor chain. Broken into different categories, the inventors contemplate: (1) a segmented, flexible chain of one or more electrical devices, (2) a method of manufacturing the same, and (3) articles of clothing incorporating the same.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Unless the context dictates the contrary, all ranges set forth in this application should be interpreted as being inclusive of their endpoints and open-ended ranges should be interpreted to include only commercially practical values. Similarly, all lists of values should be considered as inclusive of intermediate values unless the context indicates the contrary.

As used in the description in this application and throughout the claims that follow, the meaning of "a," "an," and "the" includes plural reference unless the context clearly dictates otherwise. Also, as used in the description in this application, the meaning of "in" includes "in" and "on" unless the context clearly dictates otherwise.

Broadly, a flexible segment of the chain (which will be referred to as a "chain segment" for simplicity) includes a number of key components. The chain segment includes at least one electrical device. Connected to the electrical device is a set of wires. Optionally included is a connector, which would be connected to the electrical device by the same wires. All of these components are coupled with a flexible material by injection molding such that the wires are arranged in a pattern to facilitate strain relief when the flexible material is stretched.

When fully assembled, these components make up a chain segment that includes at least one electrical device (e.g., a sensor), a connector, and a length of wires held into a strain relief pattern that couples the electrical device to the connector. Two examples can be seen in FIG. 15, which shows chain segments 1500, 1501 having multiple electrical devices 1502, 1504, 1506, 1512, 1514 and multiple connectors 1510, 1508, 1516, 1518. The electrical devices, connectors, and wires 1520, 1522 are all coupled to a flexible material by one or more different materials (e.g., silicone or plastic material). These materials can be injection molded in such a way as to encase the electrical devices 1502, 1504, 1506, 1512, 1514, the connectors 1510, 1508, 1516, 1518, and the wires. The end result is a highly flexible chain segment that can undergo large amounts of strain without breaking, experiencing significant wear, or substantially impeding movement.

Figure 1:
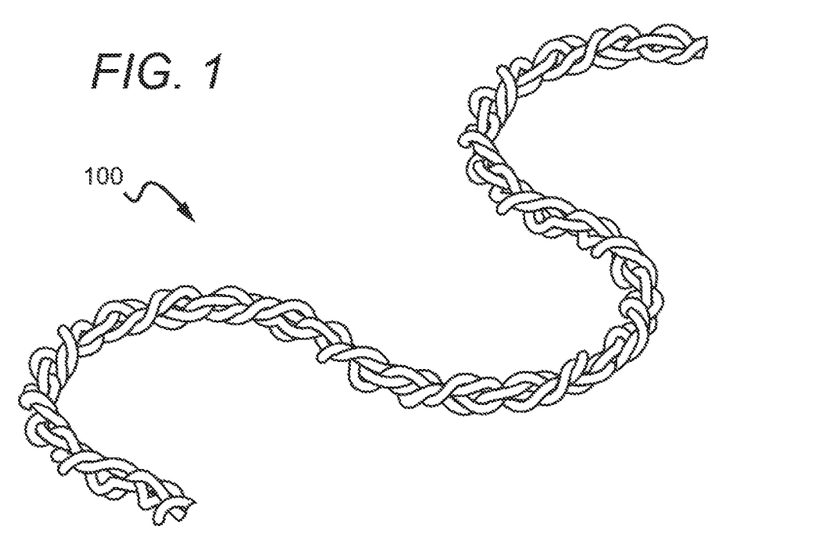
FIG. 1 shows an example of how the wires (100) connecting to the electrical device(s) can be bundled.
Figure 2:
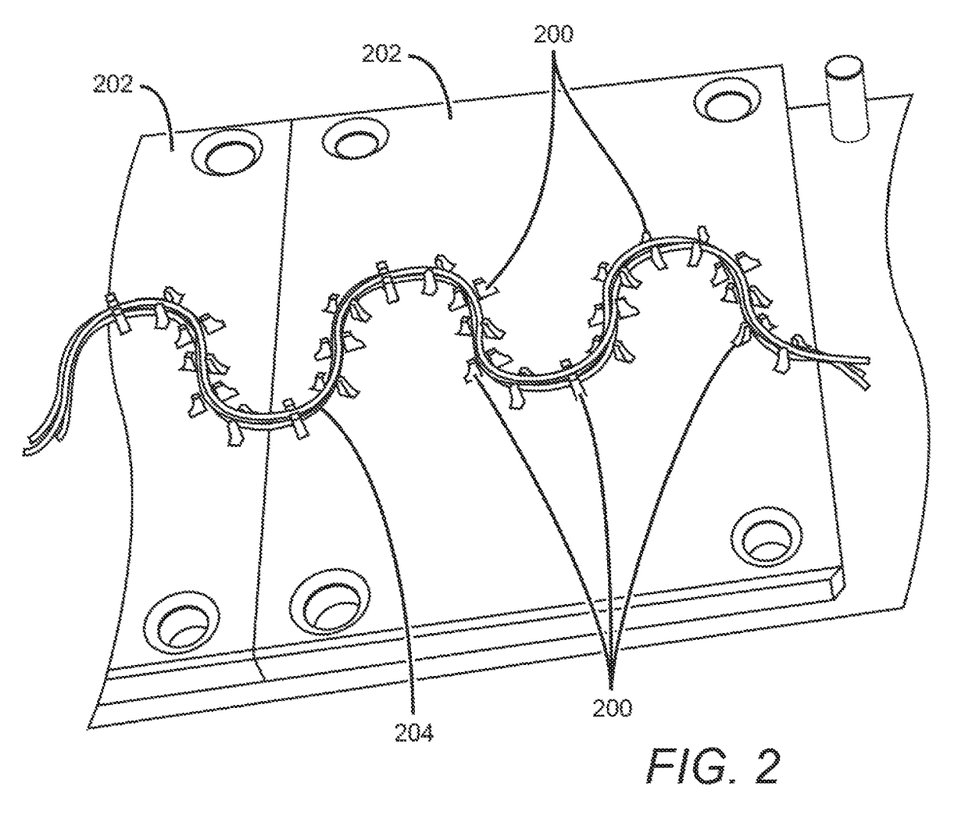
FIG. 2 shows the bundled wires held in place in a wire mold module.

Preferred chain segments incorporate as many wires (e.g., 32 American Wire Gauge with 60 strands of copper per wire) as required to connect to the electrical device (e.g., 1, 2, 3, 4, 5, 6 or more, depending on the number of pins the electrical device includes and the type of electrical device implemented). Where applicable, any place where wires are discussed in the plural can also be interpreted to encompass discussion of a singular wire. First, wires are preferably bundled together as seen in FIG. 1, although bundling is a feature of some alternate embodiments. Wires can be braided, twisted, or manufactured within a unified package. Turning now to FIG. 2, bundling the wires 204 facilitates placement of the wires 204 placed into protrusions 200 (i.e., guideposts) on the wire mold modules 202. Wire mold modules 202 having protrusions 200 are used to facilitate injection molding while the wires 204 are held in a particular pattern. The protrusions come in sets of two and preferably have a small raised portion between them to help suspend the wires 204 from the surface of the wire mold module 202. This helps to improve the encasing of the wires 204 by the injection molded material that encases the wires.

In FIG. 2, the wires 204 are held into a repeating S-shaped pattern. The pattern can also be a repeating Z-shaped pattern, or any reasonable variation of those two patterns. The purpose of the pattern is to enable strain relief, so that when the wires 204 are coupled to a piece of flexible material (e.g., a piece of fabric) and that flexible material is stretched, the wires do not break or experience significant wear (e.g., deformation that would lead to breakage after a number of cycles that would be normally experienced in the course of stretching the flexible material in the same way a garment would be stretched during normal use). In some embodiments, the wires 204 can have between a 0.008 and 0.022 in (preferably 0.016 in) outer diameter and a minimum bend radius of between 0.04 and 0.1 in (preferably 0.08 in).

Many different types of electrical devices can be used in the chain segment. An electrical device can be a single integrated circuit (IC) component, or it can be two or more IC components in communication with one another, either by a physical connection or a wireless one. As an example, an electrical device can be a sensor.

It is contemplated that a sensor in this application can be an inertial measurement unit (IMU). An IMU is a sensor package (e.g., comprising 0, 1, 2, or 3 accelerometers, 0, 1, 2, or 3 gyros, and 0, 1, 2, or 3 magnetometers, but having at least one of those three). An IMU containing 3 accelerometers, 3 gyros, and 3 magnetometers was custom developed and built by NextGen Aeronautics around an MPU-6500 COTS sensor. This custom IMU weighs ~5 grams. The sensor can communicate via, for example, and RS 485 serial connection. Each sensor can also be wirelessly equipped to enable the wireless transmission of data.

An electrical device can also be: a resistive bend sensor, an optical proximity sensor, a capacitive stretch sensor, a stitched stretch sensor or a hall effect magnetic sensor. It should be understood that anywhere this application uses the term "sensor," "IMU," or "electrical device," these terms can be interchanged with one another without departing from the inventive concepts described in this application.

The inventors contemplate that many different types of alternate sensors can be used in conjunction with IMUs or other electrical devices. A primary goal of an alternate sensor could be to provide independent angular measurements to serve as a reference frame for a more robust IMU. Alternate sensors can also simply provide information that other electrical devices do not provide. An alternate sensor can be any of the same sensors as described above with respect to electrical devices.

Because one of the purposes of the inventive subject matter is to create a sensor chain that can be incorporated into clothing to sense and record the wearer's movements, each IMU can incorporate a complementary or Kalman filter to fuse multiple sensor types and extend kinematic data to joint angles and position. IMUs can also state classification based on kinematic data to distinguish between various activities such as sitting, walking, running, climbing, etc.

In some embodiments, the electrical device is "potted." Potting is the process of sealing a component with a plastic compound or material to exclude moisture, prevent short circuits, and provide strain relief. Electrical devices as used in the chain segment are typically potted before being encased in a separate material (e.g., a silicone or plastic) that holds the electrical device to the flexible material. This process is described in more detail below.

After being potted (or in lieu of being potted, in some embodiments) an electrical device is encased in another material by injection molding. Encasing the electrical device in a material by injection molding after potting (or in lieu of potting) serves to further protect the electrical device and also to ensure the electrical device and the wires are held together by the injection molded material. It is preferable for the material injection molded around the electrical device to be similar to the material injection molded around the wires such that blending can occur where the two materials meet and mix within the molds. This blending ensures a strong connection between the wires and the electrical device, and it can also prevent tangling of the wires during compression as well as more evenly distributed strain in the wires during stretching.

Figure 14:
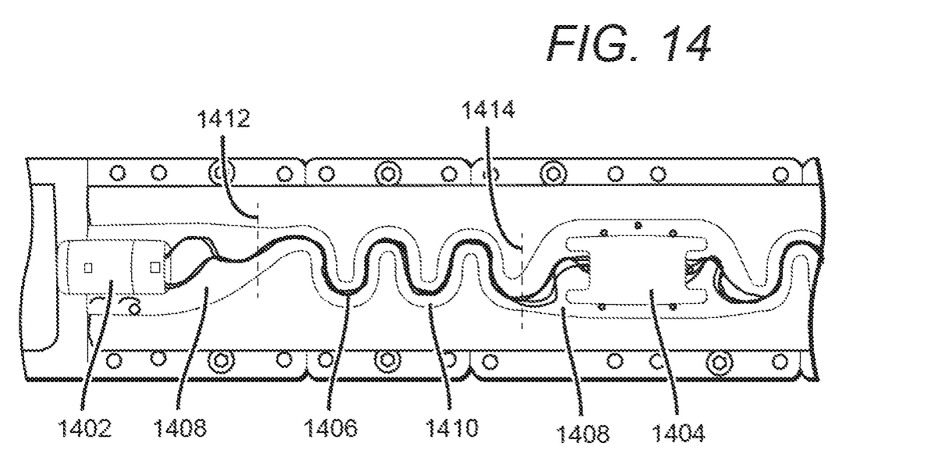
FIG. 14 shows a connector and a sensor connected by wires in a strain relief pattern after injection molding.

While one end of the chain segment has an electrical device, the other end of that segment (e.g., coupled to the opposite end of the set of wires) can be a connector. FIG. 14 shows an example of an embodiment having a connector 1402 and an IMU 1404 that are coupled by a set of wires 1406. In this embodiment, the connector 1402 and the IMU 1404 are encased in a first silicone that, when set, is harder than a second silicone 1410 encasing the set of wires.

In these embodiments, the connector 1402 can be any connector known in the art (e.g., a standard serial or parallel connector). When assembled, the connector 1402 in the chain segment can be encased in a material such as an injection molded silicone 1408. This protects the connector 1402 and softens any hard edges of the connector 1402 and protects the connector 1402 from damage from impact and other wear and tear.

Similar to an electrical device (e.g., IMU 1404), a connector 1402 is also encased in a material by injection molding. Injection molding material around the connector 1402 helps to ensure that the connector and the wires 1406 are held together by the injection molded materials 1408, 1410. It is preferable for the material injection molded around the connector 1402 to be similar to the material injection molded around the wires 1406 such that blending can occur where the two materials meet (e.g., at dotted lines 1412 and 1414) and mix within the molds. As with the electrical devices, this blending ensures a strong connection between the wires and the electrical device.

The connector 1402 can enable the connection of other electrical devices, or it can allow for uploading and downloading data from an existing electrical device 1404 (or multiple in embodiments with more than one). For example, in some embodiments, one of the electrical devices can be a system on a chip (SoC) or even a small computer, which can collect and pre-process data before offloading it via a connector. Although a connector can be used to establish an external connection, the inventors also contemplate that data can be uploaded and downloaded wirelessly (e.g., via Bluetooth, WiFi, or the like) by an electrical device that is configured for wireless communications.

Figure 15:
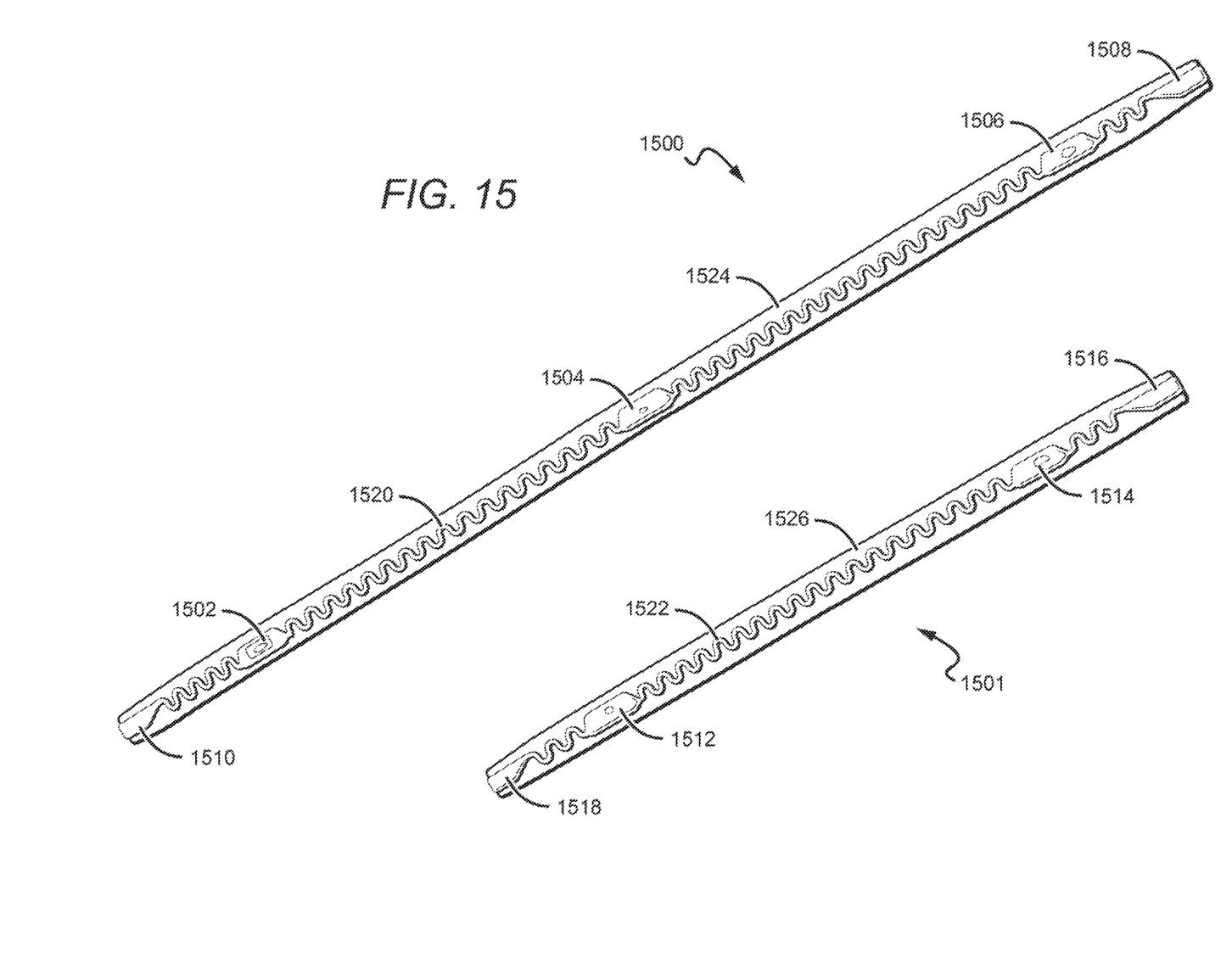
FIG. 15 shows two example flexible sensor chains having different lengths.

The inventors also contemplate that more than one electrical device (e.g., IMU) can be used to create longer chains, some examples of which are seen in FIG. 15. When multiple electrical devices 1502, 1504, 1506 are used, each electrical device can be connected to another electrical device by the wires 1520. In some embodiments, a connector 1510 is implemented as an end piece (e.g., to one or both ends of the chain), but in other embodiments no connector is used at all. Thus, a chain (e.g., 1500 or 1501) including multiple electrical devices could be arranged as: an electrical device connected to a set of wires, that set of wires connected to a second electrical device which is connected to another set of wires on its other side. Each chain can also include a flexible material 1524, 1526 which all of the aforementioned components are adhered to.

A method of manufacturing chain segments as described above is also contemplated. The method involves the use of modular molds to enable the creation of different lengths and arrangements of chain segments. Among the molds contemplated are: a wire mold module (seen in, e.g., FIGS. 2 and 11), an electrical device potting module (seen in, e.g., FIGS. 4-9), an electrical device mold module (seen in, e.g., FIG. 11), and a connector mold module (seen in, e.g., FIG. 11). This modular approach allows many different combinations of wires, electrical devices, and connectors to be arranged along a common framework and implemented to manufacture chain segments.

At a minimum, the steps to manufacture a chain segment include: (1) providing access to a wire mold module and an electrical device mold module; (2) arranging the wire mold module and the electrical device mold module according to a chain design; (3) disposing a set of wires into the wire mold module; (4) disposing an electrical device into the electrical device mold module; (5) coupling the set of wires with the electrical device; (6) injecting a material (e.g., a silicone) into the wire mold module to encase the set of wires in place; and (7) injecting another material (e.g., a silicone having the same or different material properties as the other injected material) into the electrical device mold module to encase the electrical device in place with respect to the set of wires.

Figure 3:
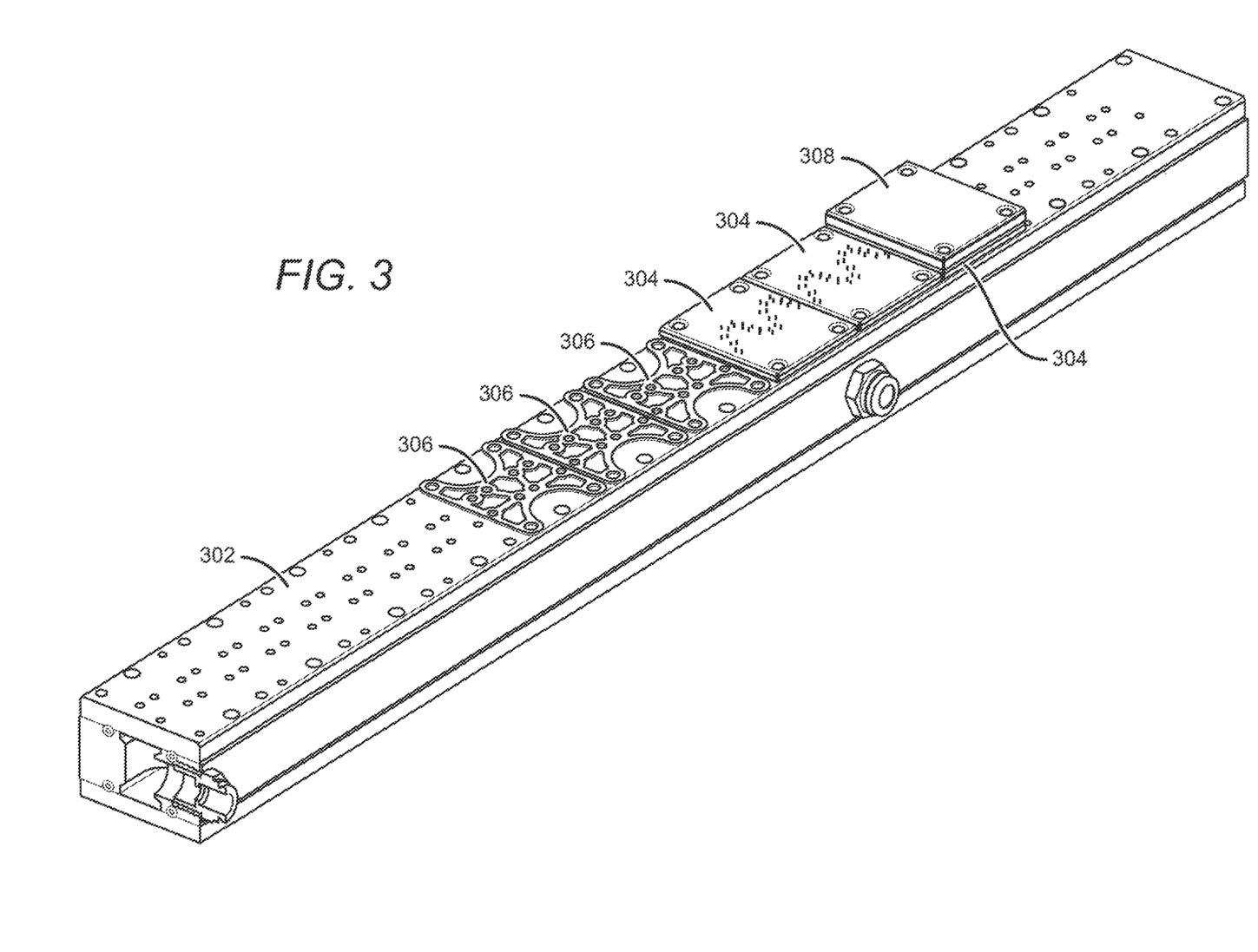
FIG. 3 shows a partially assembled injection molding apparatus.

First, wire mold module(s), electrical device module(s), and connector mold module(s) are placed in a desired arrangement along a common framework. FIG. 3 shows, for example, wire mold modules 304 in place on the common framework 302; other mold modules couple to the common framework 302 in a similar way. The arrangement of the various modules determines the length and configuration of the finished product. The common framework 302 both facilitates injection molding and enables reconfiguration of mold modules based on chain segment specifications.

Next, depending on the desired length of the chain, more than one wire mold module can be arranged next to each other. FIG. 3 shows an example embodiment where multiple wire mold modules 304 are arranged adjacent to one another along a common framework 302. This increases the amount of distance between components (e.g., electrical devices and connectors), depending on the configuration and specifications of the desired final product. It is important to note that gaskets 306 will preferably lie between a mold module (regardless of the type of mold module) and the common framework. This helps prevent unwanted leakage during high pressure injection molding.

Figure 11:
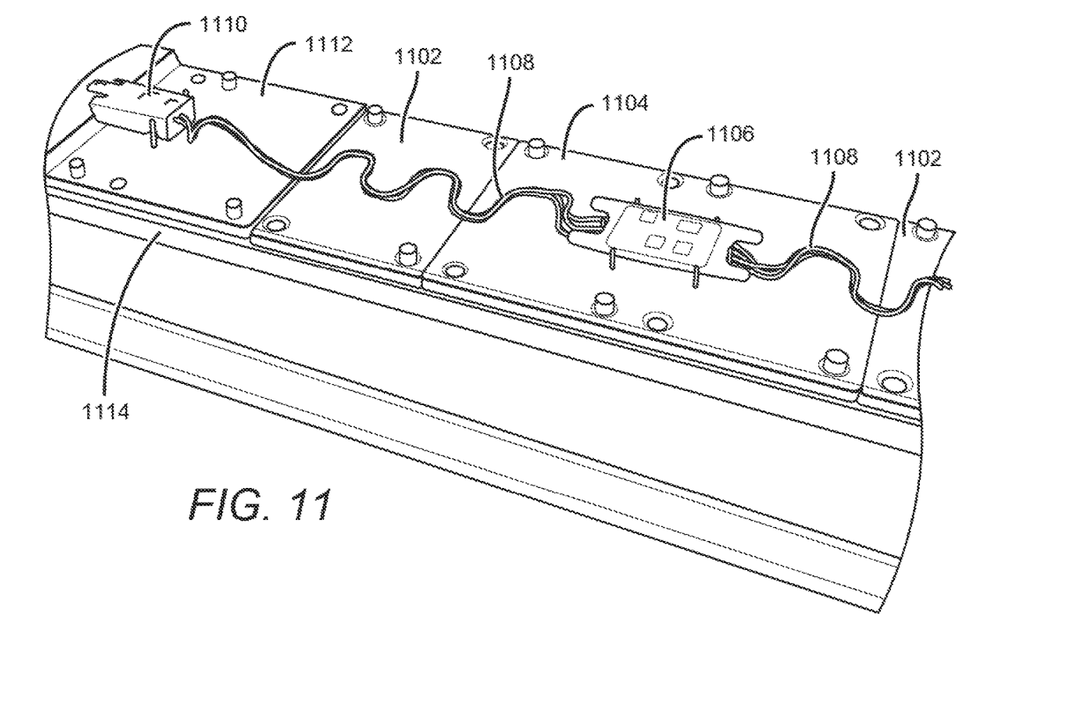
FIG. 11 shows a potted electrical device in place on an electrical device mold module.

Seen best in FIG. 11, one or more wire mold modules 1102 can be arranged in conjunction with one or more electrical device mold modules 1104 to create a desired chain segment configuration. For example, three adjacent wire mold modules can be arranged with an adjacent electrical device mold module adjacent. This configuration can additionally include a connector mold module also adjacent to the wire mold modules (e.g., the modules are ordered: 1 connector mold module, 3 wire mold modules, 1 electrical device mold module).

Next, wires are held into place in wire mold modules. FIG. 3 shows three wire mold modules, one of which also shows the top portion 308 that is used to seal the module for injection molding (for all intents and purposes, all discussion of mold modules is intended to encompass all components of the mold module, including top pieces or any other necessary parts). To create a chain segment as described above, a set of wires that connect to an electrical device must be placed into the protrusions of a wire mold module, as shown in FIG. 2. Preferably (and as described above), the wires 204 are bundled first so that they are easier to keep within the protrusions 200, though bundling is an optional feature. In embodiments where the wires are bundled, the wires can be braided, twisted, or bundled in any other practical way. Preferably, the protrusions 200 of the wire mold modules 202 come in pairs of two so that the wires 204 are held between them, and they can also include a small raised portion between each pair of protrusions 200 to create some space between the wires 204 and the surface of the wire mold modules 202. This can improve the effectiveness of the step of injection molding by helping the injection molded material surround the wires on all sides.

Once the wires are held into a pattern to facilitate strain relief (e.g., an S-shaped pattern as shown in FIG. 2, in a Z-shaped pattern, or in another pattern designed to relieve strain) by the protrusions of the wire mold modules, the top portions of the wire mold modules can be put into place to create a cavity in which a material can be injection molded to encase the wires.

Figure 4:
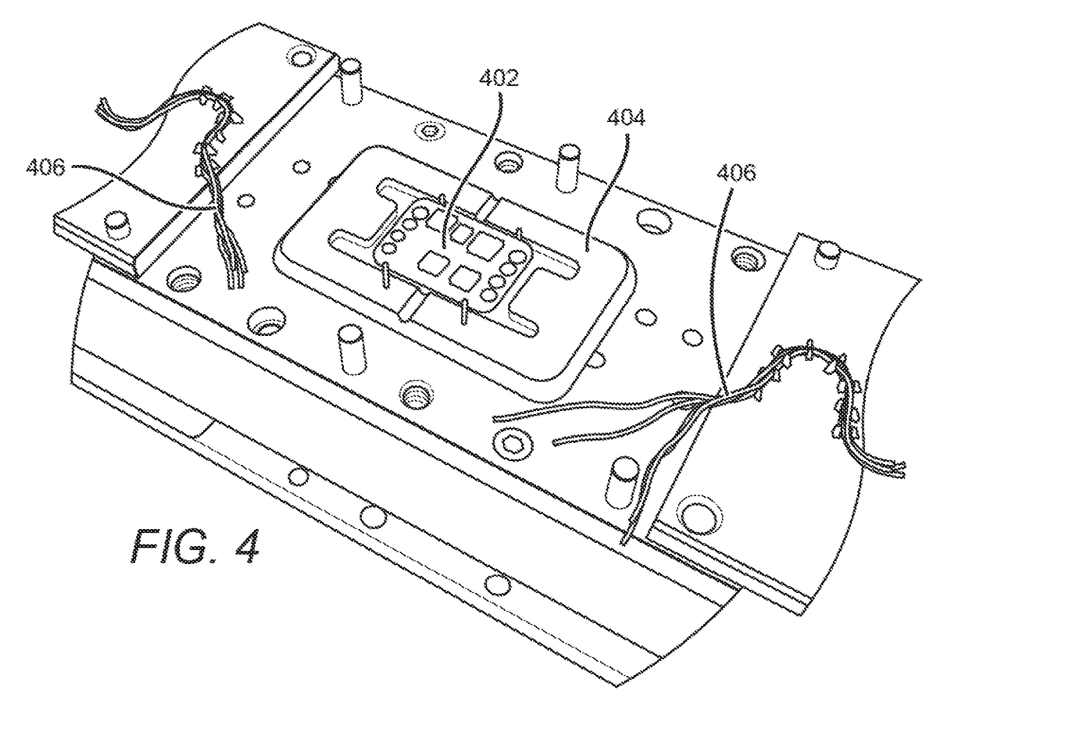
FIG. 4 shows an electrical device in a potting mold without the wires attached.
Figure 5:
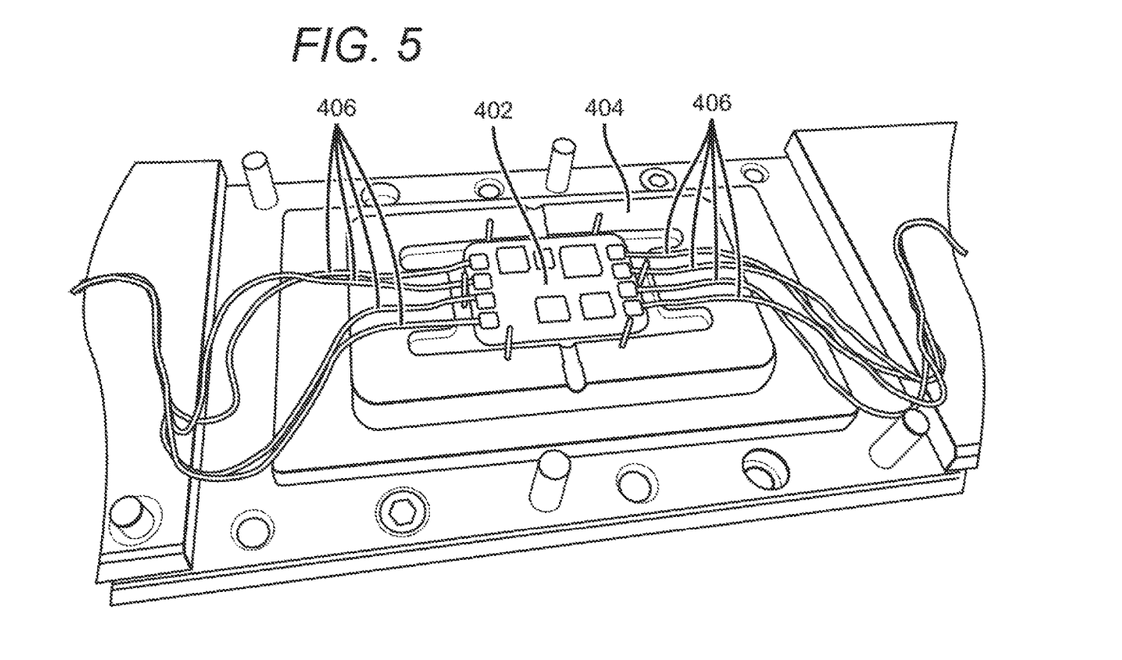
FIG. 5 shows an electrical device in a potting mold with the wires attached.
Figure 6:
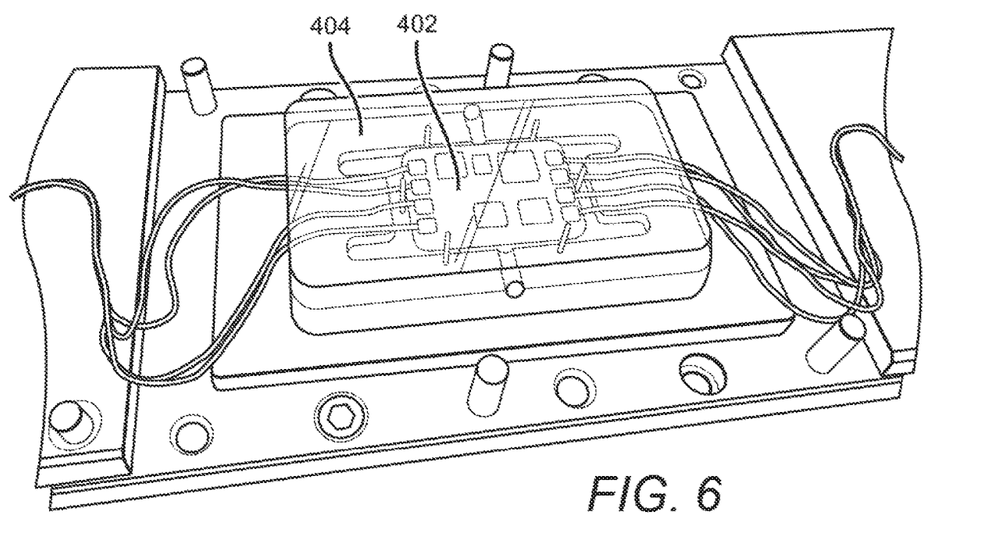
FIG. 6 shows an electrical device in a potting mold.
Figure 7:
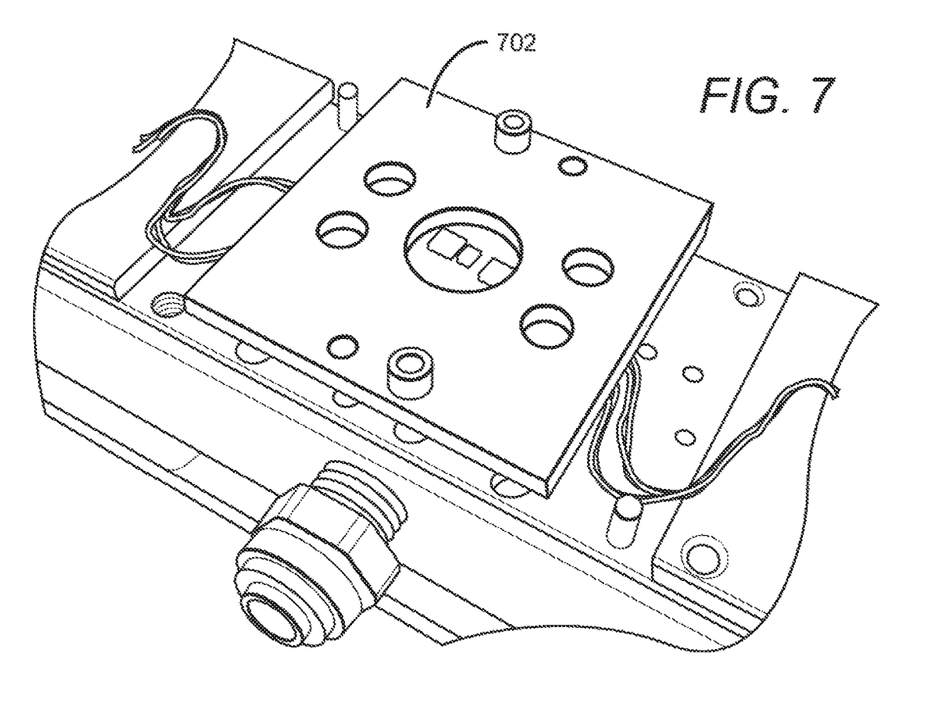
FIG. 7 shows an electrical device in a potting mold ready for injection.
Figure 8:
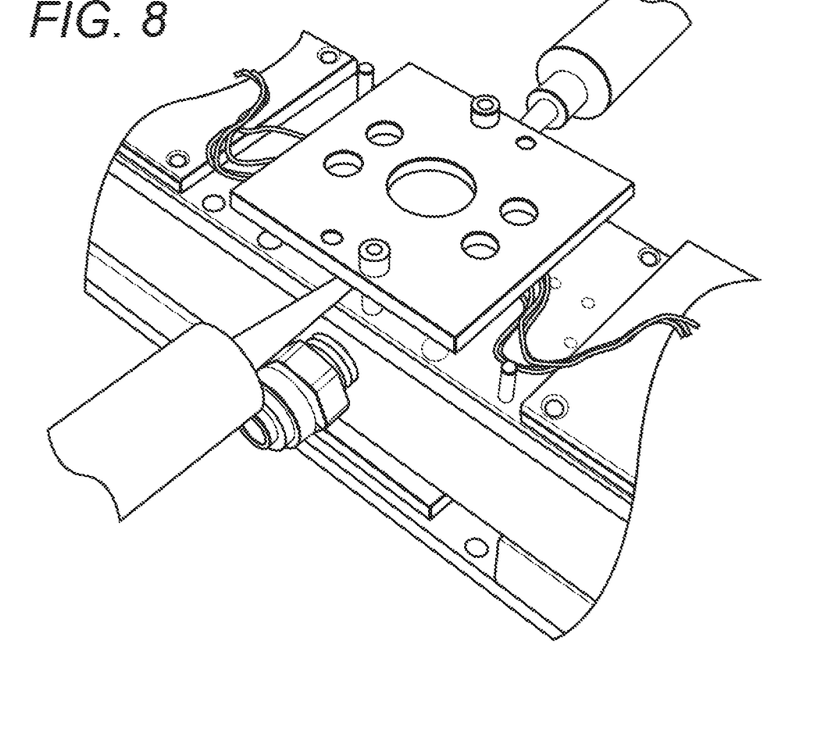
FIG. 8 shows injection of a material into the potting mold.

Next, the wires are coupled to an electrical device to prepare for injection molding that will encase the electrical device. Encasing an electrical device can be a two step process. First, the electrical devices can be "potted." FIGS. 4-10 show various stages of the potting process. FIG. 4 shows an IMU 402 placed in a potting mold 404, with wires 406 not yet connected to it. The potting mold 404 defines the shape of the potted IMU. But before the IMU 402 can be potted, the wires 406 must be connected, and FIG. 5 shows the IMU 402 in the potting mold 404 with the wires 406 connected. Next, FIG. 6 shows the IMU 402 with the potting mold 404 surrounding it. FIG. 7 shows the potting mold held in place by a sealing plate 702. And FIG. 8 shows a material (e.g., a silicone, an electronics epoxy, or some other plastic material) being injected into the potting mold.

Figure 9:
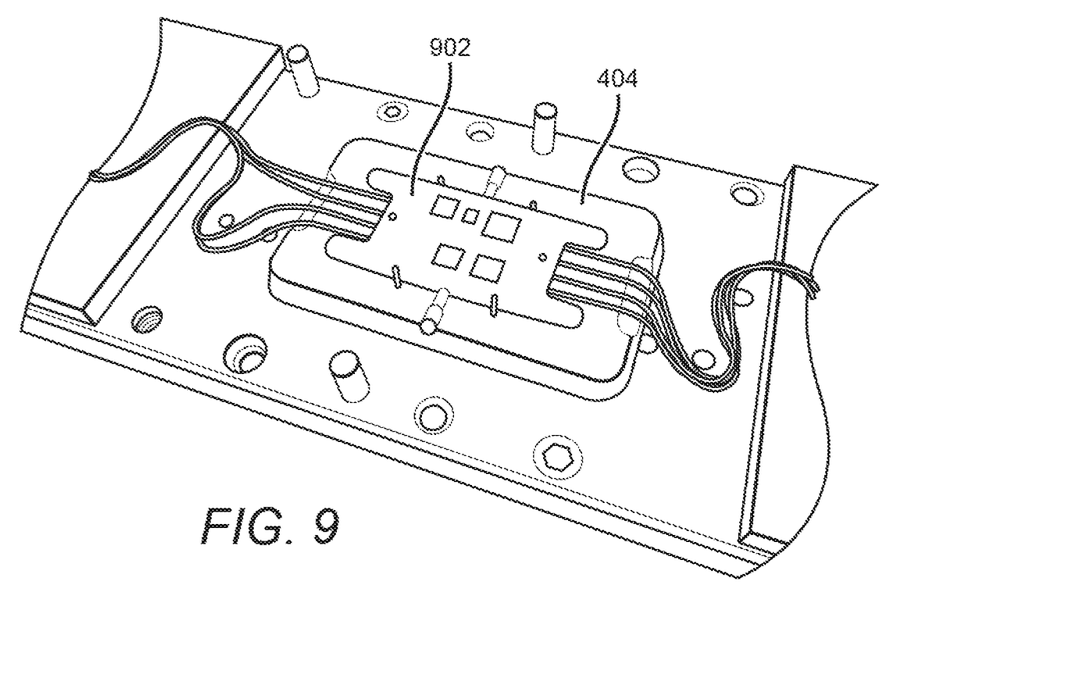
FIG. 9 shows a potted electrical device still resting in half of the potting mold.
Figure 10:
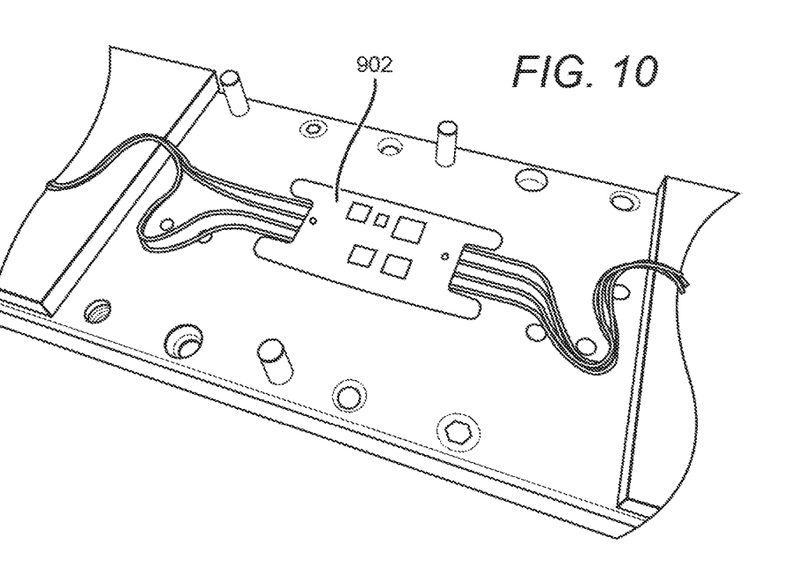
FIG. 10 shows a potted electrical device.

FIG. 9 shows a potted IMU 902 still resting in the potting mold 404, and FIG. 10 shows the potted IMU 902 in a completed state. Once potted, the IMU is protected from things like water, sweat, and other environmental elements that can cause damage. It is additionally more resistant to impact damage.

After potting (or instead of potting), an electrical device is then placed in an electrical device mold module in preparation for injection molding, as seen in FIG. 11. Encasing the electrical device 1106 in a material by injection molding after potting (or in lieu of potting, since in some cases electrical devices are not potted) serves to protect the electrical device 1106 and also to ensure the electrical device 1106 and the wires are held together by the injection molded material. As a note, FIG. 11 shows a potted electrical device, but as mentioned above, potting is an optional feature and an unpotted electronic device could be substituted in. In embodiments where potting is not performed and the electrical device is instead encased only in a single material (e.g., a silicone rubber), the electrical device is disposed in an electrical device mold module 1104 and wires 1108 are then connected to it. The order that the wires 1108 are connected to the electrical device 1106 is not critical, as long as the wires 1108 are connected prior to molding.

Next, a connector can optionally be incorporated into a chain segment, as shown in FIG. 11. The step to include a connector 1110 is similar to the step to include an electrical device. As described above, a connector mold module 1112 is placed along the common framework 1114 adjacent to a wire mold module 1102 (as pictured) or an electrical device mold module 1104. A connector can be placed into the connector mold module and wires can then be connected to it. Notably, wires 1108 can be connected at any time prior to injection molding.

As with electrical devices, in embodiments with a connector, once the connector 1110 is coupled with the wires 1108 and placed in a connector mold module 1112, the connector mold module 1112 can be sealed for injection molding to encase the electrical device 1106. An encased connector is both better coupled with the wires (e.g., to prevent breakage or slow wear and tear) and it is protected from damage.

(6) Injecting a Material

Figure 12:
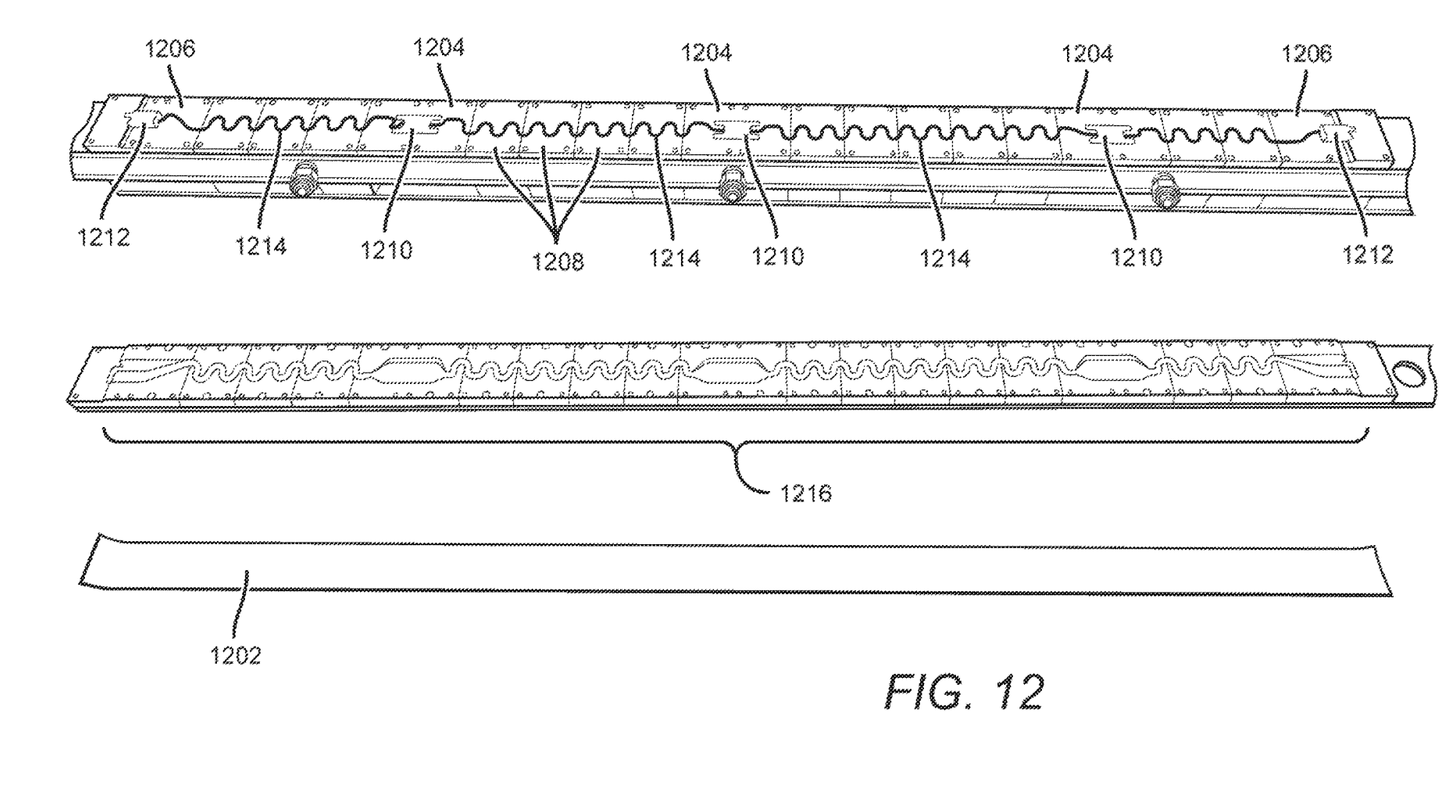
FIG. 12 shows a chain in place on the common framework for injection molding.

FIG. 12 shows all of the mold modules (e.g. electrical device mold modules 1204, connector mold modules 1206, and wire mold modules 1208) and components (e.g. electrical devices 1210, connectors 1212, and wires 1214) are in place. As seen in FIG. 12, a piece of flexible material 1202 is placed in proximity to the components (e.g., on top of the components, as shown). An example of a flexible material that can be used is a fabric weighing 5.3 oz/yrd. This fabric can be water repellant, so it will not uptake water or sweat and become heavier. The flexible material should be able to take up silicone to improve adhesion between the flexible material and the components that have been encased by injection molding. Other acceptable flexible materials include materials made from elastics, materials woven to create flexibility from stiff fibers, Lycra and Lycra-like materials, and neoprene and neoprene-like materials.

Figure 13:
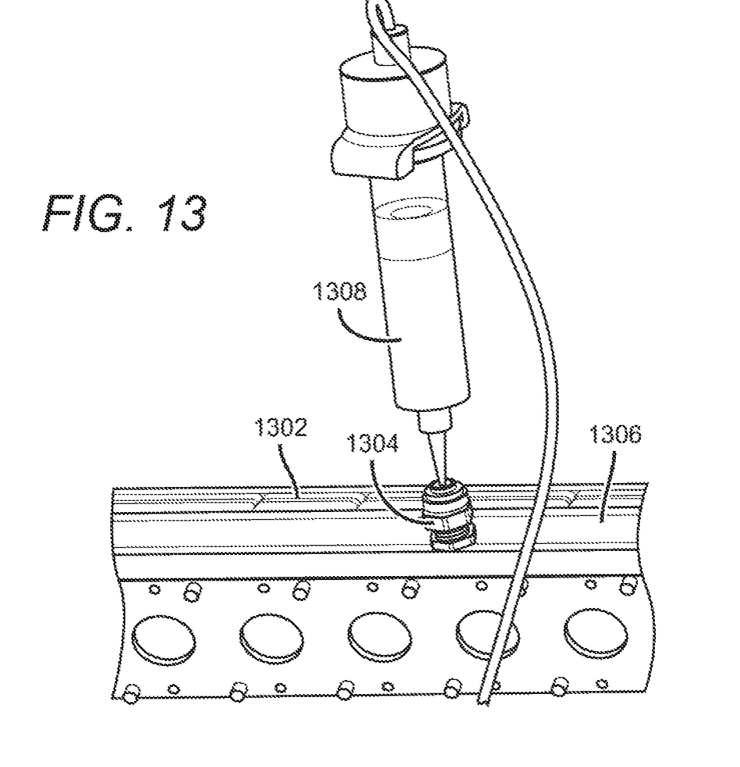
FIG. 13 shows the step of injection molding into a mold module.

Once arranged with all components in place, the mold modules are sealed using the corresponding top pieces of each mold module 1216 so that injection molding can take place. Each of the mold modules is sealed to create a cavity for injection molding such that, in some embodiments, different materials can be injection molded into different mold modules. FIG. 13 shows an example of an electrical device mold module 1302 having a first material 1308 injection molded into it via an injection port 1304.

In some embodiments, a first material is injected into the electrical device mold modules, a second material is injected into the wire mold modules, and a third material is injected into the connector mold modules. While these materials can all have different material properties, it is contemplated that any combination of the same or different materials can be injection molded into each of the mold modules.

In some chain segments, the material encasing the connectors and the electrical devices is harder than the material encasing the wires. As an example, in preferred embodiments of the chain segments, the electrical devices, connectors, and wires are encased in an injection molded silicone. It can be preferable for the silicone encasing the electrical devices to be harder than the silicone encasing the wires, since the wires must be able to stretch and deform. On the other hand, the electrical devices do not stretch and a harder silicone can help to prevent damage. The same is true for the connectors: a harder silicone material can help prevent damage. In some embodiments, the same material is used for all of the electrical devices, connectors, and wires, but any combination of relative hardnesses and materials can be used for those three components.

For example, in some embodiments, a first material (e.g., a silicone rubber) is injected into the electrical device mold module(s) and a second material (e.g., a silicone rubber softer than the first material) is injected into the wire mold modules. A third material (e.g., a silicone rubber having the same material properties as the first or second materials or a silicone rubber having still different material properties from either the first and second materials) can be injected into the connector mold modules.

The first, second, and third materials can exhibit a number of different material properties. For example, the materials can have a shore A hardness of 10 A, 15 A, 20 A, 25 A, 30 A, 35 A, 40 A, 10-15 A, 15-20 A, 20-25 A, 25-30 A, 35-40

A, or 45-50 A. The materials can have a tensile strength of 450-460 psi, 460-470 psi, 470-480 psi, 480-490 psi, 490-500 psi, or 500-510 psi. The materials can have an elongation at break percent of 300-350%, 350-400%, 400-450%, 450-500%, 500-550%, 550-600%, 600-650%, 650-700%, 700-750%, 750-800%, 800-850%, 850-900%, 900-950%, 950-1000%, 1000-1050%, or 1050-1100%. The materials can also have a die B tear strength of 100-105 pli, 105-110 pli, 110-115 pli, 115-120 pli, 120-125 pli, 125-130 pli, 130-135 pli, 135-140 pli, 140-145 pli, or 145-150 pli. The injection molded materials are ideally resistant to tearing and able to stretch considerably without experiencing excessive wear and tear.

It is contemplated that it will be preferable for the injection molded materials to be similar such that some degree of blending can occur where the different injection molded material meet. In this way, when the different injection molded materials have different material properties, there will not be an inherent weak point (e.g., a seam or other kind of joint) due to the injection molding process. In some embodiments, the different materials have the same material properties (or some combination of the same and different material properties between the three different materials) and the blending can be shown by a blending of colors. Even when the blending materials have the same material properties, the blending of colors can be useful to enable someone to visually inspect the resulting product for quality (e.g., the appearance of color blending indicating adequate injection of material).

As mentioned above, FIG. 13 shows an example of a first material being injected into the common framework 1306 such that an electrical device is encased in the first material 1308. The common framework 1306 can be configured to include multiple electrical devices that are all simultaneously encased in a first material. Injection molding can occur at high pressure (e.g., 80-90 psi, 90-100 psi, 100-110 psi, 110-120 psi) to ensure consistent results (e.g., low amounts of air bubbles or other inconsistencies that can arise during injection molding).

After injection molding, the injection molded material or materials should be allowed to cure. In some embodiments, curing can be conducted in a pressurized chamber at around 40 psi (e.g., within 5 psi of 40 psi). This helps to prevent the presence of voids in the finished product. Different injection methods can also be used including very high pressure injection (e.g., within +/−10% of 3000 psi) with heat curing to improve manufacturing speed.

Two examples of the resulting end products can be seen in FIG. 15. Both chains shown in FIG. 15 are held to a flexible piece of material 1524, 1526 by the injection molded materials.

Figures 16, 17:
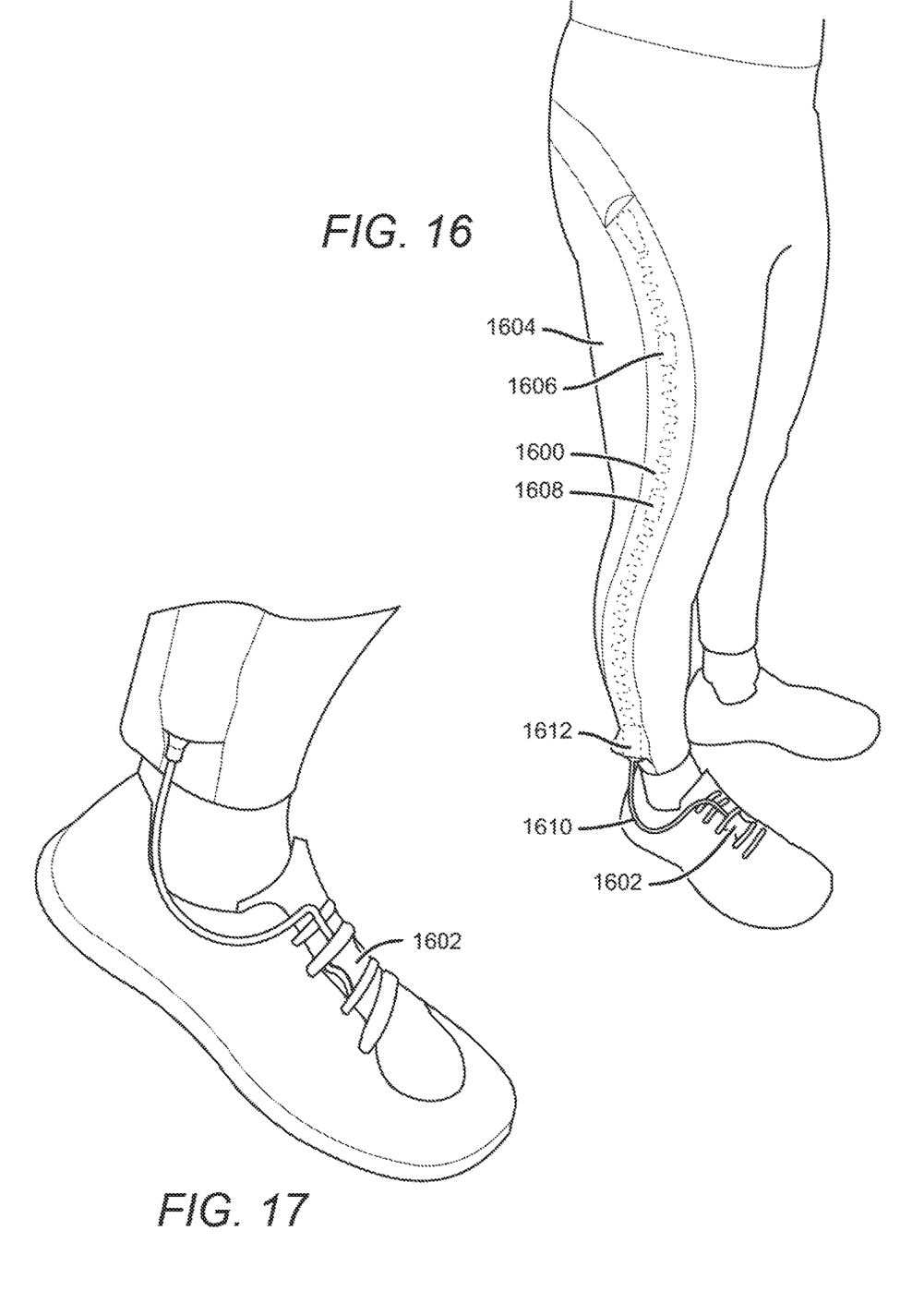
FIGS. 16-17 show an example of apparel incorporating a flexible sensor chain with a shoe sensor.

Once the product is completed, it can be incorporated into articles of clothing and other materials or products that can benefit from, for example, detection and sensing of movement. Accurate detection of movement depends in part on the location of the electrical devices (e.g., IMUs) with respect to the wearer's joints. Taking, for example, the chain segment 1600 (shown in dotted lines since it is beneath a layer of fabric) incorporated into the pair of pants 1604 as seen in FIG. 16. In embodiments where the electrical devices are IMUs, ensuring that the IMUs are in areas of low relative motion can improve long term performance (e.g., locations mid way between the joints and on the foot such as electrical device 1606). So in some embodiments, the electrical devices are located mid way between the wearer's joints (e.g., locations of low relative motion such as between the ankle and the knee, between the knee and the hip, and on the foot).

In other embodiments, it is preferable for the electrical devices to be located close to the wearer's joints (e.g., at the knee, at the hip). For example, electrical device 1608 is located near the knee in FIG. 16. In still further embodiments, electrical devices can be located in both sets of locations (as in FIG. 16), or in any subset of those locations that is preferable (e.g., at the hip, at the thigh, at the calf, and optionally at the foot, or any combination thereof). Including more IMUs can introduce a useful redundancy in the event one of the sensors fails.

The required length of the chain segment depends on the size of the garment, the length of a wearer's legs, etc. Based on the size of the garment and the person wearing the garment, chain segments can be made to be shorter or longer (for example per the method described above by including more or fewer wire mold modules with longer or shorter sets of wires). This customization enables the chain segment to be stitched into articles of clothing of any size or shape with the electrical devices located in desired regions based on the size of the clothing and also the size of the wearer.

In other embodiments, the chain segment can be incorporated into garments for the upper body. In these embodiments, the same principles apply: electrical devices can be located on and/or between joints. It is also contemplated that embodiments of the invention can be incorporated into sporting and non-sporting clothing alike.

In some embodiments, the chain segment can additionally include an electrical device (e.g., a sensor) to track movement of a person's feet. FIGS. 16-17 show example foot sensors 1602 that can connect to the chain segment via a wire 1610 that couples to the chain segment's connector 1612. A foot sensor 1602 can be, for example, an IMU as described above.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

As used in this application, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts in this application. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A segment of a chain of electrical devices that is semi-flexible, comprising:
    a first electrical device;
    a first set of wires coupled to the first electrical device, wherein the first set of wires is arranged in a bundle, and wherein the bundle is at least partially encased in a first material; and
    wherein the first set of wires are at least partially affixed to a flexible material to form a pattern to enable strain relief when the flexible material is stretched.

2. The segment of a chain of electrical devices that is semi-flexible of claim 1, wherein the first electrical device is a sensor.

3. The segment of a chain of electrical devices that is semi-flexible of claim 1, wherein the first electrical device is further encased in a second material.

4. The segment of a chain of electrical devices that is semi-flexible of claim 3, wherein the second material is harder than the first material.

5. The segment of a chain of electrical devices that is semi-flexible of claim 1, where in the flexible material is a fabric.

6. The segment of a chain of electrical devices that is semi-flexible of claim 1, wherein the pattern is one in which the bundle forms at least one of a repeated series of S-shaped bends and a repeated series of Z-shaped bends.

7. The segment of a chain of electrical devices that is semi-flexible of claim 1, wherein the first set of wires are further coupled to a connector.

8. The segment of a chain of electrical devices that is semi-flexible of claim 1, further comprising
    a second electrical device;
    a second set of wires coupled to the second electrical device;
    wherein the second set of wires are at least partially affixed to the flexible material to form the pattern to enable strain relief when the flexible material is stretched; and
    wherein the second set of wires is also coupled to the first electrical device.

9. An article of clothing having a sensor for detecting movements of a wearer, comprising:
    a segment of a chain of electrical devices that is semi-flexible, comprising:
        a first set of wires coupled to the sensor, wherein the first set of wires is arranged in a bundle, and wherein the bundle is at least partially encased in a first material;
        wherein the first set of wires are at least partially affixed to a flexible material to form a pattern to enable strain relief when the flexible material is stretched; and
    wherein the flexible material is at least partially affixed to the article of clothing.

10. The article of clothing having a sensor for detecting movements of a wearer of claim 9, wherein the flexible material is at least partially affixed to the article of clothing such that the sensor is located a distance from at least one joint of the wearer.

* * * * *